(12) United States Patent
Wulfman

(10) Patent No.: US 8,613,721 B2
(45) Date of Patent: Dec. 24, 2013

(54) DELIVERY AND ADMINISTRATION OF COMPOSITIONS USING INTERVENTIONAL CATHETERS

(75) Inventor: Edward I. Wulfman, Woodinville, WA (US)

(73) Assignee: MEDRAD, Inc., Indianola, PA (US)

( * ) Notice: Subject to any disclaimer, the term of this patent is extended or adjusted under 35 U.S.C. 154(b) by 543 days.

(21) Appl. No.: 12/742,903

(22) PCT Filed: Nov. 14, 2008

(86) PCT No.: PCT/US2008/083690
§ 371 (c)(1),
(2), (4) Date: Aug. 27, 2010

(87) PCT Pub. No.: WO2009/065078
PCT Pub. Date: May 22, 2009

(65) Prior Publication Data
US 2010/0324472 A1   Dec. 23, 2010

Related U.S. Application Data

(60) Provisional application No. 60/988,001, filed on Nov. 14, 2007.

(51) Int. Cl.
*A61B 17/22* (2006.01)
*A61B 17/20* (2006.01)
*A61M 29/00* (2006.01)

(52) U.S. Cl.
USPC .......................... 604/96.01; 604/22; 606/128

(58) Field of Classification Search
USPC .............. 604/22, 96.01–107; 606/32–45, 128
See application file for complete search history.

(56) References Cited

U.S. PATENT DOCUMENTS

| 4,790,813 A | 12/1988 | Kensey |
| 4,844,062 A | 7/1989 | Wells |
| 5,049,132 A | 9/1991 | Shaffer et al. |
| 5,112,305 A * | 5/1992 | Barath et al. ............. 604/103.01 |
| 5,196,024 A | 3/1993 | Barath |
| 5,254,089 A | 10/1993 | Wang |
| 5,304,121 A | 4/1994 | Sahatjian |
| 5,318,531 A | 6/1994 | Leone |

(Continued)

FOREIGN PATENT DOCUMENTS

| WO | 2004028610 A2 | 4/2004 |
| WO | 2005055800 A2 | 6/2005 |
| WO | 2009012163 A1 | 1/2009 |
| WO | 2009065078 A1 | 5/2009 |

OTHER PUBLICATIONS

Pathway Medical Technologies, "International Preliminary Report on Patentability," International Bureau of WIPO, International Patent Application No. PCT/US2008/083690, filed Nov. 14, 2008, 6 pages (May 18, 2010).

*Primary Examiner* — Nicholas Lucchesi
*Assistant Examiner* — Leah Stohr
(74) *Attorney, Agent, or Firm* — Ann W. Speckman; Speckman Law Group PLLC

(57) ABSTRACT

Systems and methods for delivery of therapeutic and/or diagnostic compositions to an interventional site having diseased or newly treated tissue are provided. Integrated interventional catheter systems incorporating surfaces coated with a therapeutic composition, or tissue penetration members for scoring or disrupting tissue prior to or during administration of a therapeutic composition are provided. Infusion of therapeutic composition(s) may also be provided.

24 Claims, 2 Drawing Sheets

(56) References Cited

U.S. PATENT DOCUMENTS

| | | |
|---|---|---|
| 5,320,634 A | 6/1994 | Vigil et al. |
| 5,370,653 A * | 12/1994 | Cragg .......................... 606/170 |
| 5,484,433 A | 1/1996 | Taylor et al. |
| 5,674,192 A | 10/1997 | Sahatjian et al. |
| 5,713,848 A | 2/1998 | Dubrul et al. |
| 5,713,863 A | 2/1998 | Vigil et al. |
| 5,746,716 A | 5/1998 | Vigil et al. |
| 5,779,721 A | 7/1998 | Nash |
| 5,797,935 A | 8/1998 | Barath |
| 5,836,946 A | 11/1998 | Diaz |
| 5,843,033 A | 12/1998 | Ropiak |
| 5,860,954 A | 1/1999 | Ropiak |
| 5,873,852 A | 2/1999 | Vigil et al. |
| 5,879,361 A | 3/1999 | Nash |
| 5,882,332 A * | 3/1999 | Wijay .......................... 604/508 |
| 6,001,112 A | 12/1999 | Taylor |
| 6,024,749 A | 2/2000 | Shturman et al. |
| 6,027,514 A | 2/2000 | Stine et al. |
| 6,102,904 A | 8/2000 | Vigil et al. |
| 6,210,392 B1 | 4/2001 | Vigil et al. |
| 6,241,744 B1 | 6/2001 | Imran et al. |
| 6,299,622 B1 | 10/2001 | Snow |
| 6,331,266 B1 | 12/2001 | Powell et al. |
| 6,447,525 B2 | 9/2002 | Follmer et al. |
| 6,451,036 B1 | 9/2002 | Heitzmann et al. |
| 6,494,890 B1 | 12/2002 | Shturman et al. |
| 6,503,231 B1 | 1/2003 | Prausnitz et al. |
| 6,545,775 B1 | 4/2003 | Watanabe et al. |
| 6,558,366 B1 | 5/2003 | Drasler et al. |
| 6,565,528 B1 * | 5/2003 | Mueller ....................... 604/106 |
| 6,565,588 B1 | 5/2003 | Clement et al. |
| 6,569,147 B1 | 5/2003 | Evans et al. |
| 6,585,926 B1 | 7/2003 | Mirzaee |
| 6,623,496 B2 | 9/2003 | Snow et al. |
| 6,629,953 B1 | 10/2003 | Boyd |
| 6,638,233 B2 | 10/2003 | Corvi et al. |
| 6,638,288 B1 | 10/2003 | Shturman et al. |
| 6,666,874 B2 | 12/2003 | Heitzmann et al. |
| 6,695,830 B2 | 2/2004 | Vigil et al. |
| 6,800,085 B2 | 10/2004 | Selmon et al. |
| 6,818,001 B2 | 11/2004 | Wulfman et al. |
| 6,881,203 B2 | 4/2005 | Delmore et al. |
| 6,899,731 B2 | 5/2005 | Li et al. |
| 6,936,025 B1 | 8/2005 | Evans et al. |
| 6,939,320 B2 | 9/2005 | Lennox |
| 6,984,239 B1 | 1/2006 | Drasler et al. |
| 6,991,617 B2 | 1/2006 | Hektner et al. |
| 6,997,898 B2 | 2/2006 | Forman |
| 7,273,471 B2 | 9/2007 | Wang et al. |
| 7,344,546 B2 | 3/2008 | Wulfman et al. |
| 7,470,252 B2 * | 12/2008 | Mickley et al. ........ 604/103.02 |
| 2004/0006370 A1 | 1/2004 | Tsugita |
| 2004/0098014 A1 | 5/2004 | Flugelman et al. |
| 2005/0228417 A1 | 10/2005 | Teitelbaum et al. |
| 2005/0250672 A9 | 11/2005 | Speck et al. |
| 2006/0020243 A1 | 1/2006 | Speck et al. |
| 2006/0217680 A1 | 9/2006 | Barath |
| 2008/0103446 A1 | 5/2008 | Torrance et al. |
| 2009/0018501 A1 | 1/2009 | YYribarren et al. |

* cited by examiner

DELIVERY AND ADMINISTRATION OF COMPOSITIONS USING INTERVENTIONAL CATHETERS

FIELD OF THE INVENTION

The present invention relates to the delivery and administration of therapeutic and/or diagnostic compositions to treat diseased tissue. The invention relates, more particularly, to the delivery and administration of therapeutic and/or diagnostic compositions prior to, during or subsequent to an intervention, such as displacement or removal of obstructions and partial obstructions from an internal lumen or cavity of a mammalian subject, and to interventional catheters for delivery of such compositions.

BACKGROUND

Angioplastic techniques for creating and enlarging openings in obstructed or partially obstructed blood vessels by inflating a balloon or another device at or near the site of an occlusion using an interventional catheter are well known and commonly employed. Material forming the obstruction is typically compressed during angioplasty as the vessel wall is stretched to enlarge the vessel lumen. An implantable device, such as a stent, may be placed at the site to maintain or improve vessel patency. Restenosis of vessels following angioplasty and stent placement procedures is common and may require additional interventions. Drug-eluting stents were developed to retard or reduce the incidence and severity of restenosis and have been effective in many circumstances.

Removal of diseased tissue, such as atherosclerotic plaque, thrombus and other types of obstructions and partial obstructions from internal body lumens or cavities is also a well-established interventional technique. Numerous interventional catheters have been conceived and developed. Most of these systems require placement of a guiding catheter and guide wire prior to introduction of the interventional catheter and placement of the interventional catheter near the target operating site. Advanceable, rotating operating heads have been used to cut and/or abrade and/or ablate obstructions. Plaque excision devices that incorporate cutting or scraping structures operating through a window or port, or having coring or helical screw structures that operate in a recessed opening, are also used. Aspirating catheters have been used to remove diffuse material, such as thrombus. Many of these prior art systems incorporate aspiration or mechanical withdrawal systems to remove the obstructive material from the site. Some systems incorporate or are used in conjunction with mechanisms such as distal filters for preventing obstructive material from circulating in the blood stream.

Other types of material removal systems, such as excimer lasers, high intensity focused ultrasound systems, RF systems, and the like have also been devised and used. Although mechanical devices such as cutter-based and mechanical removal devices and laser and ultrasound-based systems are effective in removing diseased tissue from and opening lumens through blood vessels, it is difficult to prevent restenosis of the vessel following material removal. Thus, despite the many and varied techniques used to prevent blood vessels from becoming occluded and the successful removal of material and placement of implantable devices such as stents, prevention of restenosis following the intervention remains problematic.

Many interventional devices have infusion systems that infuse liquids such as saline, imaging compositions, or therapeutic and/or diagnostic compositions to a site of intervention prior to or during operation of the device. Delivery of therapeutic and/or diagnostic compositions in solution using conventional infusion protocols generally isn't effective for treatment of tissue at interventional sites in blood vessels because the infusate is rapidly diluted and carried away in the bloodstream. For effective therapy or diagnosis, the composition must generally remain in contact with and have an opportunity to interact with the diseased or affected tissue. Delivery of therapeutic and diagnostic compositions to interventional sites in the blood stream thus remains challenging.

Many systems have been conceived and developed for delivery of therapeutic compositions to an interventional site. U.S. Patent Publication No. US 2005/0250672 describes a composition for restenosis prevention including an antihyperplastic composition. The composition may be applied to the outer surface of a catheter for delivery. U.S. Patent Publication No. US 2006/0020243 discloses balloon catheters coated with lipophilic drugs. U.S. Pat. No. 6,939,320 discloses a medical device including an expandable substrate, such as a balloon catheter, coated with a drug, and an expandable sheath positioned over the substrate, the expandable sheath having at least one perforation that is substantially closed when the substrate and the sheath are in a compressed state and substantially open when the substrate and sheath are expanded. The drug is thus able to pass through the sheath following expansion of the substrate and sheath.

U.S. Pat. No. 6,997,898 discloses a catheter provided with multiple inflatable balloons that, when inflated, create closed delivery pockets for delivery of compositions to a defined space. PCT International Publication No. WO 2005/055800 provides a method for exposing the luminal wall of a blood vessel to a substance by deploying a drug-eluting polymer film inside the lumen of the blood vessel during or following angioplasty.

U.S. Pat. No. 5,843,033 discloses an inflatable balloon catheter having a plurality of conduits in fluid communication with a plurality of apertures on the outer surface of the balloon, whereby medications are transferred from the conduits into a surrounding vessel following inflation of the balloon. U.S. Pat. No. 6,210,392 provides a device including an inflatable balloon mounted on a catheter, the balloon having a plurality of dispensers that extend outwardly from the balloon and are in fluid communication with a fluid source. Following delivery of the balloon to a treatment area in a vessel, the balloon is inflated to embed the dispensers in the vessel wall and fluid is introduced into the treatment area. U.S. Patent Publication No. US 2004/0098014 discloses a balloon angioplasty device having a plurality of cutting elements, such as microneedles, provided on the outer surface of the balloon. The microneedles enhance dilation of an artery and may be employed to deliver a drug to a cutting region.

U.S. Pat. No. 5,196,024 discloses a balloon catheter having cutting edges located parallel to the longitudinal axis of the balloon that make longitudinal cuts in a vessel wall. During delivery, the cutting edges are covered by folds of the deflated balloon, thereby minimizing injury to the vessel wall. U.S. Pat. No. 5,320,634 describes an angioplasty device comprising an inflatable balloon having a plurality of atherotomes mounted on its outer surface, the balloon being mounted on a catheter.

SUMMARY

The present invention provides systems and methods for effectively delivering therapeutic and/or diagnostic compositions to a site in a body lumen or cavity. In some embodiments, delivery of therapeutic and/or diagnostic composition(s) is provided in conjunction with a procedure employing an interventional catheter for delivering a device such as a balloon, or an implantable device such as a stent, to a site in a body lumen or cavity. In alternative embodiments, delivery of therapeutic and/or diagnostic composition(s) is provided in conjunction with a procedure involving an interventional catheter that removes unwanted material from a site in a lumen or cavity using a mechanical mechanism such as a cutter assembly, or a scraping mechanism or coring or helical screw mechanism, or employing a different ablative mechanism such as a laser, a high frequency ultrasound source, a radio frequency (RF) source, or a thermal or electrical source, or the like. Such systems and methods may be effectively employed to remove unwanted material from a treatment site in a body lumen and to deliver therapeutic and/or diagnostic composition(s) to the treatment site prior to, during and/or subsequent to the removal of unwanted material from the site.

In one embodiment, a delivery device of the present invention may be provided as a stand-alone delivery device, while in alternative embodiments, delivery devices of the present invention may be incorporated into or integrated with interventional devices such as interventional catheters used in angioplastic techniques, for placement of implantable devices, or for material removal (e.g., atherectomy and thrombectomy). In embodiments in which the delivery device is provided as a stand-alone device, a fluid delivery mechanism is generally provided at a distal end of an infusion lumen that may be connected to an infusate source. The delivery device may be designed for use in tandem with or as a rapid exchange device in connection with another interventional device and may share certain control and/or power functions with the interventional device. Alternatively, the delivery device may be incorporated into and integrated with an interventional device, such as an interventional catheter, that additionally provides mechanisms for angioplastic techniques, for placement of implantable devices, or for removal of unwanted material from a body lumen or cavity.

Delivery systems of the present invention generally provide a surface or a structure that contacts tissue at the site of intervention. Different mechanisms may be used for delivery of therapeutic and/or diagnostic compositions. In one embodiment, the delivery system of the present invention employs a device, such as an inflatable device, that is coated with a therapeutic and/or diagnostic composition. Various formulations for coating or impregnating or associating compositions with surfaces, providing release or uptake of the compositions are known and may be used with methods and systems of the present invention. An inflatable device may be guided to a desired treatment site in a collapsed condition and then inflated at the treatment site to contact tissue being treated and/or diagnosed. The therapeutic and/or diagnostic composition(s) are contacted to and taken up by the tissue rather than being diluted and carried away by the bloodstream or other fluids in proximity to the site.

The inflatable delivery device may incorporate blades or pins or other types of surface protuberances or abrasives or rough edges on its outer surface that produce fissures or channels or discontinuities in the tissue as the device contacts tissue to enhance uptake of the therapeutic and/or diagnostic composition(s). The inflatable delivery device may additionally or alternatively incorporate pores or ports that, upon inflation, allow passage of fluids containing therapeutic and/or diagnostic substances. The inflatable device may additionally or alternatively incorporate structures such as microneedles that provide channels for delivery of fluids containing therapeutic and/or diagnostic substances. The microneedles may penetrate tissue at a site of intervention when the inflatable device is inflated to deposit therapeutic and/or diagnostic fluids under the exposed surface or within tissue at the site of the intervention. Inflation of the device may be monitored and adjusted to provide a desired degree of penetration. The inflatable device is generally maintained in a stationary condition during inflation and contacting of its outer surface(s) to the treatment site but, in alternative embodiments, the inflatable device may be rotated and/or translated and/or vibrated during inflation and/or during contacting of its outer surface(s) and/or the structure(s) associated with the inflatable device to the treatment site.

In another embodiment, a delivery system of the present invention may employ tissue contacting and/or penetration structures that may be moved in relation to the tissue to produce fissures or channels or discontinuities in the tissue and thereby enhance the uptake of therapeutic and/or diagnostic compositions at the site of intervention. According to one embodiment, tissue contacting and/or penetration structures may be provided on an interventional device, such as on an operating head or a cutting blade of an interventional device. In this embodiment, as the operating head and/or cutting blade(s) are moved (e.g. rotated and/or translated) during an interventional procedure, the tissue contacting and/or penetration structures score the obstructive material and produce fissures and discontinuities at the site of intervention. Application of a diagnostic or therapeutic composition(s) to the disrupted tissue improves uptake of the composition(s).

According to another embodiment, tissue contacting and/or penetration structures may be provided on a supporting structure in a bristle-like or brush-like arrangement that may be adjustable between a smaller delivery condition and an enlarged treatment condition. Bristle-like contacting and/or penetration structures may be mounted in a stationary condition on a support structure, or they may be mounted for movement in relation to their support structure. In one embodiment, for example, bristle-like structures are mounted for pivoting or rotation about their attachment points on a support structure or, alternatively, single penetration structures or groups of penetration structures may be movable with or without requiring movement of a support structure.

In one embodiment, the tissue contacting and/or penetration structures may be coated with therapeutic and/or diagnostic compositions that are released during contact with tissue. In another embodiment, therapeutic and/or diagnostic compositions may be infused through channels provided in or associated with the tissue contacting and/or penetration structures, or through other infusion ports provided in proximity to the structures. The tissue contacting and/or penetration structures may be rotated and/or translated during application of the therapeutic and/or diagnostic composition(s), or they may be maintained in a stationary condition.

Therapeutic and/or diagnostic composition delivery systems of the present invention may be integrated with various types of interventional devices. Tissue contacting and/or penetration structures may be provided, for example, on an inflatable device such as a balloon. In one embodiment, the delivery systems disclosed herein are integrated with an interventional catheter comprising a distally located material removal assembly operably connected to a rotatable drive shaft and associated with a catheter assembly providing lumen(s) for aspiration and/or infusion, and suitable drive and control systems. Many types of interventional devices, including atherectomy and thrombectomy devices, tissue ablation devices, and the like, may incorporate delivery systems of the present invention, such as an inflatable device and/or tissue contacting and/or penetration structures for the delivery of a therapeutic and/or diagnostic composition.

These and additional features of the present invention and the manner of obtaining them will become apparent, and the invention will be best understood, by reference to the following more detailed description.

DETAILED DESCRIPTION

Figure 1:
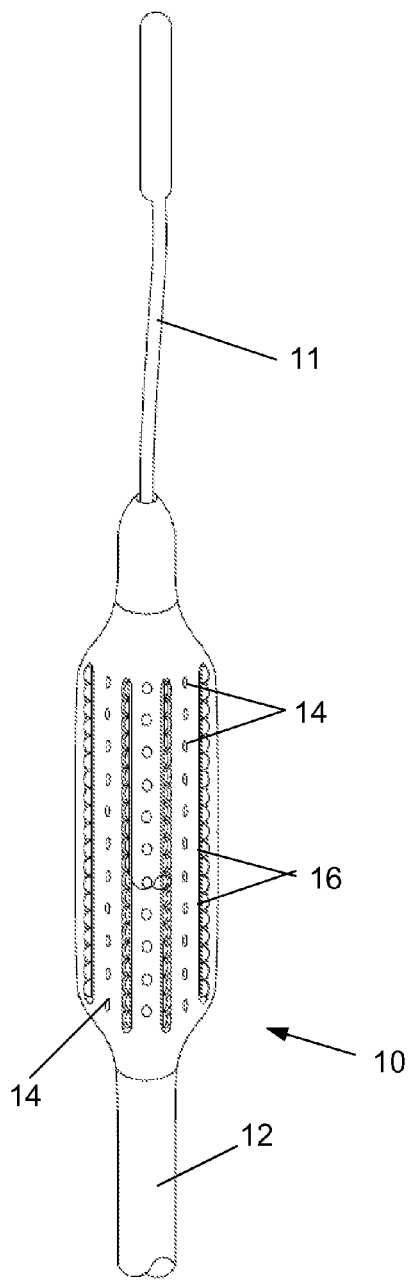
FIG. 1 shows a schematic diagram illustrating a side view of an inflatable structure having infusion ports and tissue contacting surfaces adapted to produce discontinuities in tissue when the balloon is inflated.

As outlined above, the present invention provides systems and methods for delivery of therapeutic and/or diagnostic compositions to a site of intervention. Delivery of therapeutic and/or diagnostic composition(s) using methods and structures of the present invention may be effectively combined with interventional procedures and devices for displacing or removing unwanted material from a treatment site in a body lumen, such as balloon angioplasty and/or stent placement procedures and devices, with atherectomy and thrombectomy procedures and devices, and with other material removal and lumen enlarging procedures and devices.

Body lumens and cavities in which such systems and methods may be effectively employed include blood vessels and vascular cavities, gastrointestinal cavities, lumens or cavities in male and female reproductive organs, other fluid cavities such as gas exchange cavities, nasal and sinus cavities, and the like. The lumen or cavity may be a generally tubular-shaped structure, such as blood vessel, including but not limited to, peripheral arteries or blood vessels, or another lumen structure, such as a ureter, a fallopian tube, a nasal passageway, and other tubular passageways. For example, systems disclosed herein may be used for removing undesired material from, and for delivering therapeutic and/or diagnostic compositions to, native blood vessels such as native coronary, renal, cranial, peripheral and other blood vessels, artificial or grafted vessels such as saphenous vein grafts, and the like. The body cavity may be within, or in proximity to, an organ, such as a kidney, gall bladder, lung, or the like, or the body cavity may form part of another system, such as a lymph node, spinal canal, etc. The disclosed systems are generally used with mammalian subjects, particularly human patients. The undesired material that is removed or displaced using the systems disclosed herein may be disease material such as atherosclerotic plaque, calcified plaque, thrombus, gallstones, a valve or portion thereof, and the like.

According to some embodiments, methods and systems for delivering therapeutic and/or diagnostic composition(s) are used in combination with methods and systems for creating and enlarging openings in obstructed or partially obstructed lumens or cavities using angioplastic techniques, with or without the placement of implantable devices such as stents, including drug-eluting stents. Angioplastic techniques and systems, implantable devices such as stents and drug-eluting stents are well known in the art.

According to alternative embodiments, methods and systems for delivering therapeutic and/or diagnostic composition(s) are used in combination with methods and systems for removing material from a site of intervention, such as various types of ablation systems using RF energy, high frequency ultrasound energy, lasers, high pressure fluids, thermal or electrical energy, and the like. These types of devices and systems are well known in the art.

According to yet additional embodiments, methods and systems for delivering therapeutic and/or diagnostic composition(s) are used in combination with methods and systems for removing material from a site of intervention using an interventional catheter employing a coring or cutter mechanism, an abrasive mechanism, a scraping mechanism, an excision mechanism, or the like. Material removal devices employing an interventional catheter having a mechanism operating within a window or a bore in an interventional catheter such as a blade or a helical screw may incorporate delivery of therapeutic and/or diagnostic composition(s) using methods and systems of the present invention. Interventional catheters employing rotatable and/or advanceable material removal assemblies having a coring or cutter mechanism, an abrasive mechanism, a scraping mechanism, an ablation mechanism or the like may also incorporate delivery of therapeutic and/or diagnostic composition(s) using methods and systems of the present invention. Illustrative interventional catheters are described, for example, in U.S. Pat. Nos. 6,027,514, 6,241,744, 6,638,233, 6,447,525, 6,299,622, 6,629,953, 6,623,496, 6,024,749, 6,638,288, 6,494,890, 6,001,112, 6,451,036, 6,666,874, 5,779,721, 5,879,361, 6,569,147, 5,713,848, 6,545,775, 6,936,025, 6,558,366, 6,984,239, 6,800,085, 5,484,433, 4,844,062 and 5,836,946. The disclosures of these patent publications are incorporated herein by reference in their entireties.

In certain embodiments, methods and systems for delivering therapeutic and/or diagnostic composition(s) are used in combination with methods and systems for removing material from a site of intervention using an interventional catheter employing an advanceable, rotatable distal cutter assembly. Advanceable, rotatable material removal systems that that may be effectively employed in the disclosed systems and methods include, but are not limited to, systems using differential cutting blades to remove unwanted material, such as those described in U.S. Pat. Nos. 6,565,588, 6,818,001 and 7,344,546, as well as U.S. Patent Publication No. US 2008/0103446, the disclosures of which are incorporated by reference herein in their entireties. In general, these types of interventional catheters incorporate a rotatable and translatable material removal cutter assembly, referred to herein as a "cutter", "cutter assembly" or "operating head" at their distal ends. In some embodiments, the cutter assembly is operably connected to a rotatable and axially translatable drive shaft and catheter system, drive system(s) and control system(s), and comprises at least one distally located cutting or abrading surface, or blade.

As used herein, "proximal" refers to a direction toward the system controls and the operator along the path of the drive shaft and catheter system, and "distal" refers to the direction away from the system controls and the operator along the path of the drive shaft and catheter system toward or beyond a terminal end of the cutter assembly. In general, interventional catheters employed in the systems and methods disclosed herein comprise a cutter assembly comprising at least one cutting surface positioned at or near the distal end of the interventional catheter system.

Although the "cutting" surfaces or blades of the interventional catheters may be sharp and may actually "cut" material at the target site, the term "cut" or "cutting," as used herein, refers to cutting, scraping, ablating, macerating and otherwise breaking down undesired material into removable particles or smaller, removable, units of material. "Cutters," "cutter assemblies," "cutting surfaces" and "blades" likewise refer to structures for cutting, scraping, ablating, macerating and otherwise breaking down material into smaller pieces. Such surfaces may be provided with abrasive materials.

In certain embodiments, the cutting surface(s) or blade(s) operate according to the principles of differential cutting. The cutting surfaces or blades are preferably substantially rigid, with multiple blades preferably being radially symmetrical. Cutter assemblies disclosed herein may comprise at least one cutting surface, and generally comprise a plurality of cutting blades. A cutter assembly may have fixed and/or adjustable blades. In one embodiment, a fixed blade cutter assembly is employed that comprises a plurality of cutting blades. Although the cutting surfaces on the fixed blade cutter assembly are not adjustable, the fixed blade cutter assembly may provide a range of cutting diameters as a consequence of a generally ovoid, or conical, external profile of the cutter assembly.

In another embodiment, a plurality of pivotable cutting blades are incorporated in an expandable cutter assembly that is navigable to the intervention site in a smaller diameter condition, adjusted to a larger diameter condition at the target site during operation, and finally withdrawn from the intervention site in a smaller diameter condition. In another aspect, cutter assemblies employed in the systems and methods disclosed herein incorporate both fixed cutting blades and pivotable, or expandable, cutting blades in a dual, or composite, cutter assembly.

The drive shaft that conveys rotation and torque from a drive system to the cutter assembly must be small enough and flexible enough to be navigated through small and tortuous passageways during navigation of the cutter assembly to the target removal site, and must have sufficient mechanical integrity to transfer high rotational and torque loads, and operate in a high vacuum, aspirate withdrawal environment. Multi-filar helical coils are used as drive shafts in many types of interventional catheters having a rotatable operating head.

In certain embodiments, interventional catheters employed in the disclosed systems and methods include an aspiration system for removal of debris from the intervention site, generally via aspiration through one or more material removal ports. Debris generated during a material removal operation is entrained in fluids (e.g. blood and/or infusate), and the aspirate fluid containing debris is removed by aspiration through the material removal port(s) and withdrawn through a sealed lumen of the interventional catheter. The sealed lumen is connectable to a vacuum source and aspirate collection system. Material removal ports may be provided, for example, in the cutter assembly or proximal, but in proximity to, the cutter assembly. In one embodiment, one or more aspiration port(s) may be disposed on or in proximity to the cutter assembly.

Liquid infusion may be provided in proximity to (e.g. at, distal to or proximal to) the cutter assembly in addition to, or alternatively to, aspiration. Infusion of liquids may be used to provide additional liquid volume for removal of debris, and/or to deliver lubricating fluids, treatment or diagnostic compositions, contrast agents and the like. Infusion of fluids in proximity to the area of a material removal operation may be desirable, as it tends to reduce the viscosity of the materials being removed, thus facilitating removal through relatively small diameter lumens. In addition, infusion of liquids reduces the volume of blood removed during a material removal operation, thereby reducing blood loss and allowing longer procedures if necessary. In embodiments where guidewires are employed, liquid infusion may also reduce guidewire friction. In certain embodiments, a sealed lumen formed between the cutter assembly drive shaft and a catheter may alternatively and selectively be used as an aspirate removal system and an infusion system. The sealed lumen may thus be selectively connectable to a vacuum source and aspirate collection system for aspiration, and an infusion source for infusion of liquids. Ports in or in proximity to the cutter assembly may thus be employed, selectively, as aspiration and infusion ports. Fluid may also, or alternatively, be infused through ports in an outer catheter sheath positioned proximal to the cutter assembly.

As used herein, the term "therapeutic and/or diagnostic composition or agent" refers to any material employed for its therapeutic or diagnostic effect(s) including naturally occurring and synthetic medicaments or chemicals, proteins, peptides, lipids, molecules or molecular fragments, genes, oligos, and other biological substances. Such compositions may be delivered in solution or suspension or emulsion formulation, with a suitable carrier, and may incorporate additional components. Such compositions may also be delivered in a gel formulation or associated with a polymer or another matrix. Therapeutic and/or diagnostic composition(s) may alternatively be encapsulated in a liposome or another structure or associated with a carrier such as a microsphere, a bead, a nanoparticle or another particle, or the like.

Therapeutic compositions that may be effectively delivered using the disclosed systems and methods include, but are not limited to, compositions that are able to inhibit or reduce or retard or substantially prevent restenosis and neointimal proliferation, promote healing, promote tissue (e.g. blood vessel) health and structure, such as thrombolytic compositions, anti-restenosis compositions, anti-aggregation compositions, anti-proliferation compositions and bioactive substances such as growth factors, wound healing compositions, etc.

More specifically, such therapeutic compositions include, but are not limited to: anti-thrombogenic compositions, such as heparin, heparin derivatives, urokinase, and PPACK (dextrophenylalanine proline arginine chloromethylketone); antioxidants, such as probucol and retinoic acid; angiogenic and anti-angiogenic compositions and factors; compositions that block smooth muscle cell proliferation, such as rapamycin, angiopeptin and monoclonal antibodies capable of blocking smooth muscle cell proliferation; anti-inflammatory compositions such as dexamethasone, prednisolone, corticosterone, budesonide, estrogen, sulfasalazine, acetyl salicylic acid and mesalamine; calcium entry blockers such as verapamil, diltiazem and nifedipine; antineoplastic/antiproliferative/antimitotic compositions such as paclitaxel, 5-fluorouracil, methotrexate, doxorubicin, daunorubicin, tacrolimus, cyclosporine, cisplatin, vinblastine, vincristine, epothilones, endostatin, angiostatin and thymidine kinase inhibitors; immunosuppressants such as sirolimus (rapamycin); antimicrobials such as triclosan, cephalosporins, aminoglycosides, and nitorfurantoin; anesthetic compositions such as lidocaine, bupivacaine, and ropivacaine; nitric oxide (NO) donors such as lisidomine, molsidomine, L-arginine, NO-protein adducts, NO-carbohydrate adducts, polymeric or oligomeric NO adducts; anti-coagulants such as D-Phe-Pro-Arg chloromethyl ketone, RGD peptide-containing compounds, heparin, antithrombin compounds, platelet receptor antagonists, anti-thrombin antibodies, anti-platelet receptor antibodies, enoxaparin, hirudin, Warfarin, Dicumarol, aspirin, prostaglandin inhibitors, platelet inhibitors and antiplatelet factors; vascular cell growth promotors such as growth factors, growth factor receptor antagonists, transcriptional activators and translational promotors; vascular cell growth inhibitors such as growth factor inhibitors, growth factor receptor antagonists, transcriptional repressors, translational repressors, replication inhibitors, inhibitory antibodies, antibodies directed against growth factors, bi- (or multi-)functional molecules comprising a growth factor and a cytotoxin, and bi- (or multi-)functional molecules comprising an antibody and a cytotoxin; cholesterol-lowering compositions; vasodilating compositions; compositions which interfere with endogenous vascoactive mechanisms; survival genes which protect against cell death, such as anti-apoptotic Bcl-2 family factors and Akt kinase; and combinations thereof.

Proteins that may be effectively delivered using the disclosed systems and methods include angiogenic factors and other molecules able to induce angiogenesis, including acidic and basic fibroblast growth factors, vascular endothelial growth factor, HIF-1, epidermal growth factor, transforming growth factor-alpha and -beta, platelet-derived endothelial growth factor, platelet-derived growth factor, tumor necrosis factor-alpha, hepatocyte growth factor and insulin-like growth factor; cell cycle inhibitors including CDK inhibitors; anti-restenosis compositions, including p15, p16, p18, p19, p21, p27, p53, p57, Rb, nFkB and E2F decoys, thymidine kinase and combinations thereof; and other compositions useful for interfering with cell proliferation, including compositions for treating malignancies. Protein fragments and peptides may be used. Polynucleotide sequences encoding such proteins and peptides may also, or alternatively, be delivered to a treatment site using the disclosed systems and methods.

Other compositions that may be delivered using the present invention include therapeutic polynucleotide sequences, such as sense and anti-sense, as well as modified and unmodified DNA and RNA molecules and fragments, DNA coding for an anti-sense RNA, or DNA coding for tRNA or rRNA to replace defective or deficient endogenous molecules, that have a therapeutic effect after being taken up by a cell.

The therapeutic and/or diagnostic composition may be formulated as a coating, in a solution or associated with a polymer or another type of matrix for infusion, and/or in a matrix or formulated on nanoparticles or in or on beads (such as nanospheres or microspheres), liposomes, or other delayed or sustained release formulations. Methods for the preparation of such formulations are well-known in the art. Various types of biocompatible matrices may be used in coating formulations. A combination of more than one therapeutic and/or diagnostic composition may be delivered to a desired treatment site. Different compositions may be delivered to the treatment site at different times prior to, during and/or following an interventional procedure.

In systems having a diagnostic and/or therapeutic composition delivery system incorporated with another interventional device, the integrated system may include an infusion manifold and at least one control feature for supplying, and controlling administration of, one or more compositions containing a therapeutic and/or diagnostic composition(s). Multiple chambers and/or infusion channels may be provided for supplying, and controlling the administration of, multiple infusate compositions. The compositions may be infused proximal or distal to an operating head or another component of an interventional catheter, and/or through ports at various locations in the interventional catheter. Therapeutic and/or diagnostic compositions may be delivered following placement of the interventional catheter before, during and/or after an interventional procedure.

In another embodiment, a therapeutic and/or diagnostic composition(s) is provided as a coating on an inflatable device, such as a balloon- or a balloon-like device, which may be guided to an interventional site in an uninflated (e.g., collapsed) state and inflated or otherwise enlarged to present a larger surface area at or near the site of intervention. A surface of the inflated device preferably contacts tissue at the site of intervention before, during or after an intervention. The inflatable device may have a generally cylindrical central region, and may have a generally oval or oblong configuration overall. In many embodiments, the inflatable device is formed from a liquid and gas impermeable material and may be constructed, for example, from thermoplastics, such as polyurethane, polyvinyl chloride, polyethylene, polypropylene, polyamides and polyesters. Fluids are generally infused to an internal cavity in the inflatable device to inflate, or enlarge, the device at the site of intervention.

Methods and materials for preparing drug-coated devices such as balloons are known in the art and include, for example, those disclosed in U.S. Pat. Nos. 5,304,121 and 5,674,192, the disclosures of which are hereby incorporated by reference. In one aspect, the disclosed systems and methods employ a balloon coated with a diagnostic or therapeutic composition, such as Paclitaxel, for example in an amount of approximately 1-10 (e.g. 3) mcg paclitaxel/mm$^2$ balloon surface. Suitable amounts of alternative diagnostic and therapeutic compositions may be determined using the knowledge of one of ordinary skill in the art and/or routine experimental protocols.

A coated inflatable device, such as a balloon, may be integrated with an interventional catheter providing another interventional structure or mechanism for delivery therapeutic and/or diagnostic composition(s) according to methods and systems of the present invention. An inflatable device coated with a therapeutic and/or diagnostic composition and an inflation mechanism, such as a fluid delivery channel may, for example, be integrated with any of the interventional or material removal devices referred to above. In one embodiment, an inflatable device coated with a therapeutic and/or diagnostic composition may be integrated with an angioplasty system, for example. In another embodiment, an inflatable device coated with a therapeutic and/or diagnostic composition may be integrated with an implantable device system such as a stent placement system. In yet another embodiment, an inflatable device coated with a therapeutic and/or diagnostic composition is integrated with a material removal system, such as an aspiration catheter, a plaque excision system or a rotational atherectomy or thrombectomy system.

The coated inflatable device may be positioned proximal or distal to an operating head of the interventional device during use, and may be mounted on, or integrated with, a dedicated inflation sheath associated with the interventional catheter. Alternatively, the coated inflatable device may share a fluid inflation lumen with the interventional catheter, with the fluid lumen serving as both an infusion and inflation lumen.

The coated inflatable device may be enlarged to contact the therapeutic and/or diagnostic composition(s) provided on its surface to the surface of tissue at or near the site of intervention before, during and/or after an interventional operation. In one method, for example, the interventional catheter is first employed to open a pathway at a treatment site in a body lumen or cavity, and the interventional catheter is subsequently repositioned so that the inflatable balloon is located in proximity to the treatment site. The balloon is then inflated (or otherwise enlarged) so that at least part of the balloon's outer surface contacts the inner wall of the lumen or cavity, whereby the therapeutic and/or diagnostic composition contacts the lumen wall. The balloon may remain stationary during contact with the lumen or cavity, or it may be vibrated or otherwise moved against the inner wall of the lumen or cavity. The balloon may alternatively or additionally be employed to deliver a therapeutic and/or diagnostic composition before use of the interventional catheter, or the balloon may be employed after removal of the cutting assembly from the treatment site.

In another embodiment, which may be employed alternatively to or in conjunction with a coating on an inflatable device, the inflatable device may be constructed from a porous material or comprise one or multiple pores. In this embodiment, a therapeutic and/or diagnostic composition may be formulated in and carried by the fluid used to inflate the balloon, such that the therapeutic and/or diagnostic composition "weeps" from the balloon when it is enlarged, and is thereby delivered to the treatment site. Multiple compositions may be delivered to a site of intervention through a single inflatable device at different times using this technique. Methods and materials for the constructing such porous balloons are well known in the art and include those described in U.S. Pat. Nos. 6,585,926, 5,318,531, 5,049,132, 5,860,954 and 5,254,089, the disclosures of which are hereby incorporated by reference in their entireties.

Inflatable devices employed in the systems and methods disclosed herein may also, or alternatively, be provided with one or more tissue contacting or penetration structures, such as cutting or abrading element(s) on the exposed surface that act to cut or scrape or score tissue, such as plaque, or produce fissures in the tissue during contact. Penetration or scoring of the tissue during or prior to contact with a therapeutic and/or diagnostic composition assists in delivery and uptake of the therapeutic and/or diagnostic composition. The tissue penetration structure(s) may be provided in the form of a rigid, or semi-rigid, protrusion such as a pin or protuberance or blade element, or a wire or microneedle or the like, or may be provided as an abrasive material in the form of a particulate coating, such as diamond grit or another type of abrasive material. The tissue penetration structure may be provided with a coating comprising a therapeutic and/or diagnostic composition. A plurality of microneedles may be provided on the outer surface of the balloon, as disclosed for example in U.S. Patent Publication No. US 2004/0098014, the disclosure of which is hereby incorporated by reference.

The tissue penetration structures may be substantially solid, or they may have one or more channels or conduits through which a therapeutic and/or diagnostic composition may be delivered to a site of intervention. Methods and materials for forming microneedles are well known to those of skill in the art and include, for example, those disclosed in U.S. Pat. Nos. 6,881,203, 6,331,266 and 6,503,231, the disclosures of which are hereby incorporated by reference. FIG. 1 illustrates one embodiment of an inflatable device of the present invention that may be used independently of an interventional device for delivery of a diagnostic and/or therapeutic composition prior to, during or following an intervention, or may be incorporated in an interventional assembly. Inflatable device 10 is generally provided in association with and at or near the distal end of a catheter 12 and may be translated to an interventional site on a guidewire 11. It is conveyed to the desired target site in a small diameter condition and inflated at the target site as is known in the art. The external surface of inflatable device 10 may incorporate a therapeutic composition coating, as is known in the art. The therapeutic composition coating may be provided in a generally uniform distribution over the exposed surface of balloon 10, or a drug coating may be provided in a non-uniform distribution, with higher concentrations of compositions, or different compositions, provided at different surface areas of balloon 10.

The external surface of balloon 10 may also incorporate one or a plurality of pores 14 for releasing a liquid formulation from an internal space of the balloon. The pores may have substantially uniform sizes, as illustrated, or pores having different sizes may be provided. And, pores may be provided in a regular, radially arranged distribution, as shown in FIG. 1, or they may be provided in an irregular pattern over the surface area of the balloon. Pores 14 are illustrated on the substantially cylindrical surfaces of balloon 10 in FIG. 1, but pores may alternatively, or additionally, be provided on the tapered end walls of balloon 10.

Balloon 10 additionally comprises a plurality of tissue contacting surfaces 16 adapted to produce discontinuities or small fissures in tissue when the balloon is inflated. Tissue contacting surfaces 16 may be relatively sharp or relatively benign to tissue, and they may be coated with a diagnostic and/or therapeutic substance. They may be provided in generally uniform sizes and in a regular arrangement, as illustrated in FIG. 1, or tissue contacting surfaces may have non-uniform sizes and shapes, and they may be provided in an irregular arrangement over the surface area of the balloon. Tissue contacting surfaces may comprise particulate materials, such as grit (e.g. diamond grit) having various particle sizes.

The balloon may be delivered to a target intervention site for treatment independent of another intervention, or for treatment prior to, during, and/or following another interventional procedure. Upon delivery to the target site, the balloon is enlarged sufficiently so that at least a portion of the tissue contacting surfaces 16 contact tissue at the target intervention site. An infusate comprising a diagnostic and/or therapeutic composition is preferably infused, e.g. through ports 14, during or following contacting of the tissue contacting surfaces with tissue at the target site. The balloon may be maintained in a generally stationary condition during treatment, or it may be translated or rotated or oscillated or vibrated or otherwise moved during treatment to enhance contacting of surfaces 16 with tissue at the site and to promote uptake, but tissue at the site, of the diagnostic and/or therapeutic composition(s). Multiple compositions may be infused, sequentially or simultaneously. The balloon is deflated and withdrawn from the site following the desired treatment.

Figure 2:
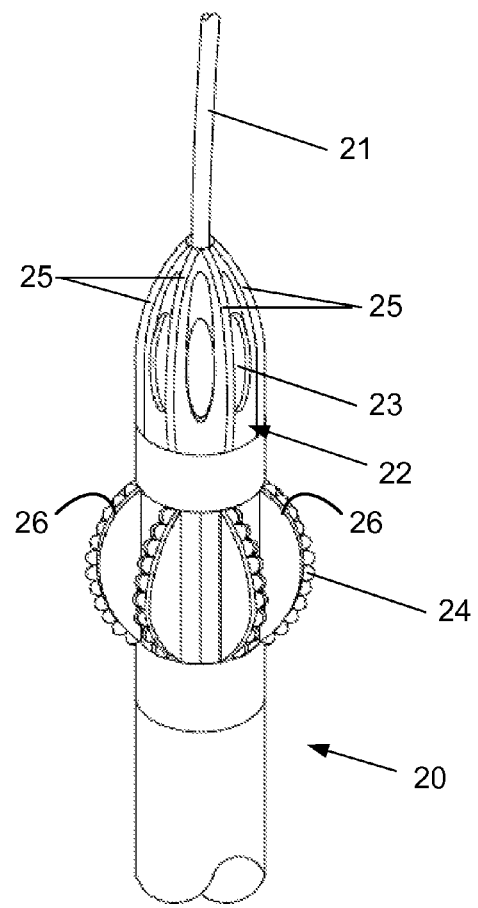
FIG. 2 shows a schematic diagram illustrating a side view of the working head of an interventional catheter having a cutter assembly with tissue penetration structures associated with the cutter assembly.

In another embodiment, illustrated in FIG. 2, tissue penetration structures may be mounted on or associated with one or more components of an interventional device, such as one or more blades of a cutter assembly. FIG. 2 illustrates an exemplary interventional catheter 20 mounted for axial translation on guidewire 21 and comprising a distal operating head 22 having multiple, radially arranged cutter blades or surfaces 25 and multiple ports 23. Tissue penetration structures 24 are mounted on blade surfaces 26 proximal to distal operating head 22. The tissue penetration structures 24 score tissue, or produce fissures in the tissue, as the interventional device is moved (e.g., rotated and/or translated) at the site of the intervention. The tissue penetration structures may be coated with a therapeutic and/or diagnostic composition, as described above, or they may be used in conjunction with an infusion system or an inflatable device for placing the therapeutic and/or diagnostic composition(s) at the site of intervention during or following treatment of tissue. The tissue penetration structures may be mounted in a permanent and/or stationary condition, or they may be mounted for retraction during placement at or withdrawal from the site of intervention.

The tissue penetration structures mounted on or associated with a component of an interventional device, such as a cutter assembly, may be provided as serrated portions and/or abrasive or cutting structures, such as fine wires or comb-like structure(s). In one embodiment, for example, wires or comb-like structures may be mounted to or associated with surfaces of blades forming a cutter assembly of an interventional catheter. In general, the wires or comb-like structures are oriented at an angle to, and generally transverse with respect to, the surface of a blade or another interventional catheter structure and project at least a small distance from the peripheral edge of the blade or the other structure. As the blades are rotated and/or translated, the serrations and/or abrasive elements (e.g., wires or comb-like structures) create fissures or discontinuities in the tissue located on the lumen wall at the site of the intervention. These fissures improve penetration of therapeutic and/or diagnostic compositions, such as anti-restenotic drugs, that may be administered via infusion (e.g., through an integrated infusion or through a separate infusion system) or using an inflatable device, such as a coated balloon as described above. Such compositions may be delivered either prior to, simultaneously with, or subsequent to, operation of the cutting assembly.

Interventional catheters having abrasive elements and/or tissue penetration structures may be employed in combination with drug-coated and/or porous inflatable balloons, as detailed above, to improve delivery of therapeutic and/or diagnostic compositions to tissue at the site of intervention. An occluding balloon may also, or alternatively, be deployed distally to the site of intervention and the operating head of an interventional catheter system to retain a therapeutic and/or diagnostic composition in the treatment area for a sufficient time for uptake of the composition. A distal occluding balloon may, for example, be provided on a guidewire. Examples of occluding balloons that be effectively employed in the present systems and methods include those described in U.S. Pat. No. 4,790,813, the disclosure of which is incorporated by reference herein in its entirety.

In yet a further embodiment, a brush-like element comprising a number of bristle-like structures capable of scoring or producing fissures in tissue such as plaque, deposited on the inner wall of a vessel lumen, may be used to improve penetration of a therapeutic and/or diagnostic composition in tissue. The brush-like element(s) may be provided on, or integrated with, an interventional catheter, or it may be provided as a separate device and used independently from operation of an interventional catheter. In use, the bristle-like structures contact tissue at a site of intervention before and/or after use of an interventional catheter or delivery of a therapeutic and/or diagnostic composition, or may be left in place at a desired site for a period of time to maximize the therapeutic effect. The brush-like element may be used to treat tissue, for example, prior to infusion of a diagnostic and/or therapeutic composition to improve uptake of the composition(s) by the treated tissue.

The bristle-like structures preferably have a stiffness sufficient to score tissue as they are moved (e.g., rotated and/or translated) with respect to the tissue. They may be provided with an abrasive material on their outer surface, and/or they may have sharp edges. The bristle-like structures may be coated with a therapeutic composition, such as paclitaxel or rapamycin, to improve penetration of the therapeutic composition in tissue at the site of intervention and thereby increase the therapeutic effect. Alternatively, the bristle-like structures may be hollow, or may be provided with infusion channels, and a therapeutic and/or diagnostic composition may be infused through the bristle-like structures when they are positioned at a desired site, or during movement of the bristle-like structures at the site. In one embodiment, the bristles may be constructed from microporous fibers and channels provided in the fibers may be in communication with a source of infusate. Microporous fibers having, for example, an inner diameter of 0.001 inch and an outer diameter of 0.003 inch are suitable bristle-like structures.

In one embodiment, the bristle-like structures extend generally radially from, and are mounted in a fixed, stationary condition on a supporting structure. The supporting structure may comprise at least part of the outer circumference of the catheter, or it may comprise a structure separate from a catheter. In other embodiments, the bristles rotate, reciprocate and/or pivot at their attachment points. In one embodiment, the bristles of the brush-like element extend from the outer surface of the catheter at an angle that is approximately 90° to the longitudinal axis of the catheter. In other embodiments, the angle between the bristles and the longitudinal axis of the catheter is less than 90° with the tips of the bristles pointing in either a generally proximal or distal direction, and the bristles are able to pivot along a limited, generally longitudinal path. The bristles are of a sufficient length to contact the deposited material whereby, as the catheter is moved either proximally or distally, the tips of the bristles are forced into the plaque and moved from a generally proximal or distal orientation, to a generally vertical orientation and finally to a generally distal or proximal orientation.

Figure 3:
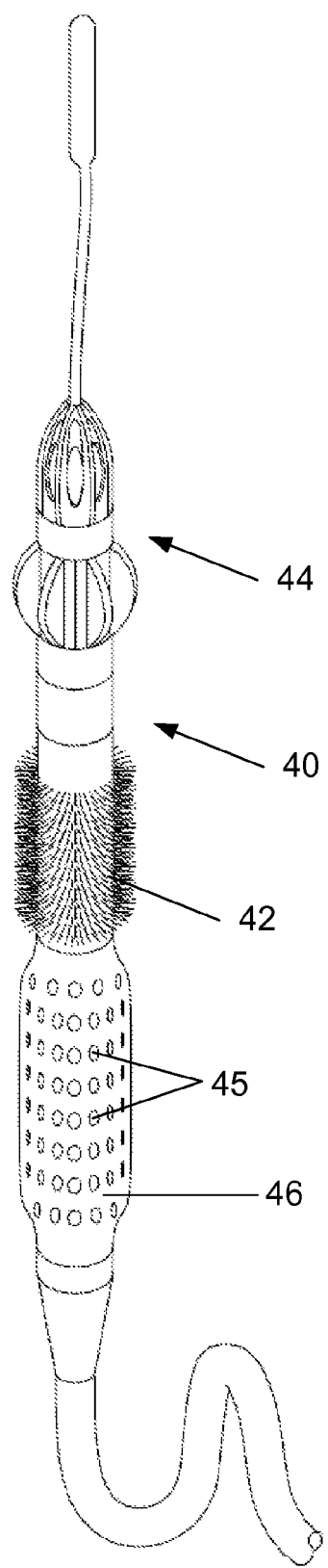
FIG. 3 shows a schematic diagram illustrating a side view of an interventional catheter assembly of the present invention incorporating a working head having a cutter assembly for removal of material from a blood vessel lumen, a brush-like element having bristles for contacting tissue at the interventional site, and infusion ports for infusion of a therapeutic composition.

In one embodiment, illustrated schematically in FIG. 3, a brush-like element 42 is provided on an interventional catheter assembly 40 generally proximal to a cutting assembly 44, with the bristles initially lying in a generally proximal orientation. The cutting assembly may be operated, first, to cut or debulk material, such as plaque, deposited on the inside of a body lumen. Following a debulking operation, the catheter may be moved distally to position the brush-like element 42 in proximity to the portion of the vessel where the intervention took place, and near exposed tissue surfaces. The catheter may then be translated in a proximal direction, whereby the bristles penetrate tissue at the site, delivering a treatment composition to the exposed tissue. Employing an interventional catheter having both a cutting assembly and a brush-like element means that both plaque removal and delivery of a therapeutic composition may be achieved by placement of a single catheter in the vessel, resulting in improved time and cost efficiency compared to the use of two catheters and reducing risk to the patient.

The interventional catheter assembly illustrated schematically in FIG. 3 additionally comprises a plurality of infusion ports 45 provided in an inflatable member 46 mounted on interventional catheter 40 proximally of the brush-like element 42. Various compositions may be infused through inflatable member 46 prior to or during an atherectomy or thrombectomy procedure, and prior to or during subsequent treatment using the brush-like element. Employing an interventional catheter having a cutting assembly, a brush-like member and one or more infusion systems provides plaque removal and effective delivery of a diagnostic and/or therapeutic composition with placement of a single catheter in the vessel, resulting in improved time and cost efficiency compared to the use of two catheters and reducing risk to the patient.

While the present invention has been described with reference to specific embodiments thereof, it should be understood by those skilled in the art that various changes may be made and equivalents may be substituted without departing from the true spirit and scope of the invention. Many alternative embodiments are disclosed, many of which may be combined in methods and systems of the present invention. In addition, many modifications may be made to adapt a particular situation, material, composition of matter, method, method step or steps, for use in practicing the present invention. All such modifications are intended to be within the scope of the claims.

All of the publications, patent applications, and patents cited in this application are herein incorporated by reference in their entireties to the same extent as if each individual publication, patent application or patent was specifically and individually indicated to be incorporated by reference in its entirety.

I claim:

1. A system for removing unwanted material from a body lumen or cavity comprising:
   (a) a catheter;
   (b) an operating head positioned at or near a distal end of the catheter;
   (c) at least one infusion port provided near the distal end of the catheter and in proximity to the operating head;
   (d) a plurality of tissue penetration members provided as bristle-like structures having a stiffness sufficient to score tissue as they are moved with respect to the tissue and located in proximity to the at least one infusion port, wherein the plurality of tissue penetration members is adapted to contact tissue within a body lumen or cavity to promote uptake of a composition infused through the at least one infusion port, and
   (e) an inflatable structure adapted to adjust from a smaller diameter delivery condition to a larger diameter deployed condition, wherein the at least one infusion port is provided in the inflatable structure.

2. The system of claim 1, wherein the at least one tissue penetration member is provided on the inflatable structure.

3. The system of claim 2, wherein the inflatable structure incorporates a plurality of surface protuberances on its outer surface that produce fissures in tissue to enhance uptake of a therapeutic and/or diagnostic composition infused through the at least one infusion port.

4. A system for removing unwanted material from a body lumen or cavity comprising:
   (a) a catheter;
   (b) an operating head positioned at or near a distal end of the catheter;
   (c) at least one infusion port provided near the distal end of the catheter and in proximity to the operating head; and
   (d) a plurality of tissue penetration members provided in conjunction with the operating head and located in proximity to the at least one infusion port, wherein the tissue penetration members are provided on the operating head as wires or comb-like structures associated with the surfaces of blades forming the operating head and are adapted to contact tissue within a body lumen or cavity to promote uptake of a composition infused through the at least one infusion port.

5. A system for removing unwanted material from a body lumen or cavity comprising:
   (a) a catheter;
   (b) an operating head positioned at or near a distal end of the catheter;
   (c) at least one infusion port provided near the distal end of the catheter and in proximity to the operating head; and
   (d) a plurality of tissue penetration members provided as bristle-like structures having a stiffness sufficient to score tissue as they are moved with respect to the tissue and located in proximity to the at least one infusion port, wherein the plurality of tissue penetration members is adapted to contact tissue within a body lumen or cavity to promote uptake of a composition infused through the at least one infusion port, and wherein the plurality of tissue penetration members is mounted on a supporting structure and adjustable between a smaller delivery condition and an enlarged treatment condition.

6. The system of claim 5, wherein the bristle-like structures are mounted for movement in relation to the supporting structure.

7. The system of claim 5, wherein the plurality of tissue penetration member is coated with a therapeutic and/or diagnostic composition that is adapted to be released during contact with tissue.

8. A method for administering a therapeutic and/or diagnostic composition to an internal lumen or cavity prior to, during or following an interventional procedure, comprising:
   (a) delivering a working head of an interventional catheter having a plurality of tissue penetration members provided as wires or comb-like structures associated with surface of blades forming the operating head to the site of the interventional procedure;
   (b) operating the working head to at least partially displace or remove an obstruction from an internal lumen or cavity;
   (c) contacting tissue penetration members mounted on the working head of the the interventional catheter to tissue at the site of the interventional procedure prior to, simultaneously with or following operation of the working head; and
   (d) administering a therapeutic and/or diagnostic composition to the site of the interventional procedure during or following contacting of the tissue penetration members to the tissue at the site of the interventional procedure.

9. The method of claim 8, wherein the therapeutic and/or diagnostic composition is administered to the site of the interventional procedure through an inflatable member having at least one infusion port.

10. The method of claim 8, wherein the site of the interventional procedure is selected from the group consisting of: blood vessels and vascular cavities, gastrointestinal cavities, lumens or cavities in male and female reproductive organs and the urinary tract, gas exchange cavities, and nasal and sinus cavities.

11. The method of claim 8, additionally comprising enlarging an opening in an obstructed or partially obstructed lumen or cavity as part of the interventional procedure.

12. The method of claim 8, wherein the working head is selected from the group consisting of ablation system using RF energy, high frequency ultrasound energy, lasers, high pressure fluids, thermal or electrical energy.

13. The method of claim 8, wherein the working head comprises a coring mechanism, a cutter mechanism, an abrasive mechanism, a scraping mechanism or an excision mechanism.

14. The method of claim 8, wherein therapeutic and/or diagnostic composition comprises a composition selected from the group consisting of: anti-thrombogenic compositions; antioxidants; angiogenic compositions and factors; anti-angiogenic compositions and factors; compositions that block smooth muscle cell proliferation; anti-inflammatory compositions; calcium entry blockers; antineoplastic compositions; antiproliferative compositions; antimitotic compositions; immunosuppressant compositions; antimicrobial compositions; anesthetic compositions; nitric oxide donors; anti-coagulants; vascular cell growth promoters; vascular cell growth inhibitors; cholesterol-lowering compositions; vasodilating compositions; compositions that interfere with endogenous vasoactive mechanisms; survival genes; and polynucleotide sequences.

15. A system for removing unwanted material from a body lumen or cavity comprising:
   (a) a catheter;
   (b) an operating head positioned at or near a distal end of the catheter;
   (c) at least one infusion port provided near the distal end of the catheter and in proximity to the operating head;
   (d) a plurality of tissue penetration members provided as bristle-like structures having a stiffness sufficient to score tissue as they are moved with respect to the tissue and located in proximity to the at least one infusion port, wherein the plurality of tissue penetration members is adapted to contact tissue within a body lumen or cavity to promote uptake of a composition infused through the at least one infusion port; and
   (e) an aspiration port in or in proximity to the operating head and an aspiration system communicating with the aspiration port for removal of debris from a site of intervention.

16. The system of claim 15, wherein the operating head comprises a material removal device employing a coring or cutter mechanism, an abrasive mechanism, a scraping mechanism, or an ablation mechanism.

17. A method for administering a therapeutic and/or diagnostic composition to an internal lumen or cavity prior to, during or following an interventional procedure, comprising:
   (a) delivering the working head of an interventional catheter to the site of the interventional procedure;
   (b) operating the working head to at least partially displace or remove an obstruction from an internal lumen or cavity;
   (c) contacting tissue penetrating structures mounted on a component of the interventional catheter to tissue remaining at the site of the interventional procedure prior to, simultaneously with or following operation of the working head, wherein the tissue penetrating structures are bristle-like structures having a stiffness to score tissue as they are moved with respect to the tissue and wherein the tissue penetrating structures are coated with a therapeutic composition; and
   (d) administering a therapeutic and/or diagnostic composition to the site of the interventional procedure during or following contacting of the tissue penetrating structures to the tissue at the site of the interventional procedure.

18. The method of claim 17, wherein the working head comprises a coring mechanism, a cutter mechanism, an abrasive mechanism, a scraping mechanism or an excision mechanism.

19. A method for administering a therapeutic and/or diagnostic composition to an internal lumen or cavity prior to, during or following an interventional procedure, comprising:
   (a) delivering the working head of an interventional catheter to the site of an interventional procedure, wherein the working head is selected from the group consisting of ablation system using RF energy, high frequency ultrasound energy, lasers, high pressure fluids, thermal or electrical energy;
   (b) operating the working head to at least partially displace or remove an obstruction from an internal lumen or cavity;
   (c) contacting tissue penetrating structures mounted on a component of the interventional catheter to tissue remaining at the site of the interventional procedure prior to, simultaneously with or following operation of the working head, wherein the tissue penetrating structures are bristle-like structures having a stiffness to score tissue as they are moved with respect to the tissue; and
   (d) administering a therapeutic and/or diagnostic composition to the site of the interventional procedure during or following contacting of the tissue penetrating structures to the tissue at the site of the interventional procedure.

20. The method of claim 19, wherein the tissue penetrating structures are hollow and additionally comprising administering a therapeutic and/or diagnostic composition through the tissue penetrating structures when they contact tissue remaining at the site of the interventional procedure.

21. The method of claim 19, wherein the site of the interventional procedure is selected from the group consisting of: blood vessels and vascular cavities, gastrointestinal cavities, lumens or cavities in male and female reproductive organs and the urinary tract, gas exchange cavities, and nasal and sinus cavities.

22. The method of claim 19, additionally comprising enlarging an opening in an obstructed or partially obstructed lumen or cavity as part of the interventional procedure.

23. The method of claim 19, wherein therapeutic and/or diagnostic composition comprises a composition selected from the group consisting of: anti-thrombogenic compositions; antioxidants; angiogenic compositions and factors; anti-angiogenic compositions and factors; compositions that block smooth muscle cell proliferation; anti-inflammatory compositions; calcium entry blockers; antineoplastic compositions; antiproliferative compositions; antimitotic compositions; immunosuppressant compositions; antimicrobial compositions; anesthetic compositions; nitric oxide donors; anticoagulants; vascular cell growth promoters; vascular cell growth inhibitors; cholesterol-lowering compositions; vasodilating compositions; compositions that interfere with endogenous vasoactive mechanisms; survival genes; and polynucleotide sequences.

24. A method for administering a therapeutic and/or diagnostic composition to an internal lumen or cavity prior to, during or following an interventional procedure, comprising:
   (a) delivering the working head of an interventional catheter to the site of interventional procedure;
   (b) operating the working head to at least partially displace or remove an obstruction from an internal lumen or cavity;
   (c) contacting tissue penetrating structures mounted on a component of the interventional catheter to tissue remaining at the site of the interventional procedure prior to, simultaneously with or following operation of the working head, wherein the tissue penetrating structures are bristle-like structures having a stiffness to score tissue as they are moved with respect to the tissue; and
   (d) administering a therapeutic and/or diagnostic composition to the site of the interventional procedure during or following contacting of the tissue penetrating structures to the tissue at the site of the interventional procedure, wherein the therapeutic and/or diagnostic composition is administered to the site of the interventional procedure through an inflatable member having at least one infusion port.

* * * * *

UNITED STATES PATENT AND TRADEMARK OFFICE
CERTIFICATE OF CORRECTION

PATENT NO. : 8,613,721 B2  
APPLICATION NO. : 12/742903  
DATED : December 24, 2013  
INVENTOR(S) : Wulfman Page 1 of 1

It is certified that error appears in the above-identified patent and that said Letters Patent is hereby corrected as shown below:

IN THE CLAIMS:
Column 15, Line 35, Claim 2, delete "wherein the at least" and insert -- wherein at least --, therefor.
Column 16, Line 13, Claim 7, delete "member is" and insert -- members is --, therefor.
Column 16, Line 22, Claim 8, delete "surface" and insert -- surfaces --, therefor.
Column 16, Line 28, Claim 8, delete "the the interventional catheter" and insert -- the interventional catheter --, therefor.
Column 16, Line 50, Claim 12, delete "system" and insert -- systems --, therefor.
Column 17, Line 41, Claim 17, delete "stiffness" and insert -- stiffness sufficient --, therefor.
Column 17, Line 59, Claim 19, delete "system" and insert -- systems --, therefor.
Column 18, Line 6, Claim 19, delete "stiffness" and insert -- stiffness sufficient --, therefor.
Column 18, Line 54, Claim 24, delete "stiffness" and insert -- stiffness sufficient --, therefor.

Signed and Sealed this
Eighth Day of July, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,613,721 B2  Page 1 of 1
APPLICATION NO. : 12/742903
DATED : December 24, 2013
INVENTOR(S) : Edward I. Wulfman It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 649 days.

Signed and Sealed this

Twenty-second Day of September, 2015

Michelle K. Lee
*Director of the United States Patent and Trademark Office*